United States Patent [19]

Gray

[11] Patent Number: 5,093,257

[45] Date of Patent: Mar. 3, 1992

[54] HYBRID PROKARYOTIC POLYPEPTIDES PRODUCED BY IN VIVO HOMOLOGOUS RECOMBINATION

[75] Inventor: Gregory L. Gray, South San Francisco, Calif.

[73] Assignee: Genencor International, Inc., South San Francisco, Calif.

[21] Appl. No.: 431,705

[22] Filed: Nov. 1, 1989

Related U.S. Application Data

[63] Continuation of Ser. No. 752,267, Jul. 3, 1985, abandoned.

[51] Int. Cl.$^5$ .................. C12N 9/28; C12N 9/52; C12N 9/54; C12N 9/56
[52] U.S. Cl. ................. 435/202; 435/220; 435/221; 435/222
[58] Field of Search .............. 435/69.1, 172.3, 252.3, 435/320, 202, 220, 221, 222

[56] References Cited

U.S. PATENT DOCUMENTS 4,336,336  6/1982  Silhavy et al. ............... 435/172.3
4,469,791  9/1984  Colson et al. ............... 435/252.31
4,493,893  1/1985  Mielenz et al. .............. 435/172.3

FOREIGN PATENT DOCUMENTS 32134  7/1981  European Pat. Off. .

OTHER PUBLICATIONS

Schneider, W. P. et al., 1981, Proc. Nat'l. Acad. Sciences, USA, 78(4):2169–2173.
Tommassen, J. et al., 1985, The EMBO Journal, 4(6):1583–1587.
Weber et al., Nucleic Acids Research, vol. 11, pp. 5661–5669, 1983.
Yamane et al., In Microbiology, 1982, (ed. Schlessinger, American Society for Microbiology, Washington, D.C.), 1982, pp. 8–11.
Biswas et al., J. Bacteriol. 151(2):77–82, 1982.
Contente et al., Plasmid 2:555–571, 1979.
Ortlepp et al., Gene 23:267–276, 1983.
Thudt et al., Gene 37:163–169, 1985.
Vasantha et al., J. Bacteriol. 159(3):811–819, 1984 (Sep.).

Primary Examiner—Richard A. Schwartz
Assistant Examiner—William W. Moore
Attorney, Agent, or Firm—Flehr, Hohbach, Test, Albritton & Herbert

[57] ABSTRACT

Novel circular vectors containing a recplicable DNA sequence and DNA sequences encoding all or part of at least two distinct parental polypeptides are disclosed. Such vectors are used in novel processes utilizing in vivo recombination to produce recombined circular vectors containing said replicable DNA sequences and hybrid DNA sequences comprising: (1) a first DNA sequence encoding the amino-terminal portion of a hybrid polypeptide corresponding to a first part of a first parental polypeptide sequence and (2) a second DNA sequence encoding a carboxy-terminal portion of said hybrid polypeptide corresponding to a first part of a second parental polypeptide sequence. The hybrid DNA sequences of such recombined circular vectors can exprress novel hybrid polypeptides such as hybrid enzymes in general and in particular hybrid amylases and proteases. Various other processes are disclosed to isolate the recombined circular vector containing said hybrid DNA sequences.

12 Claims, 11 Drawing Sheets

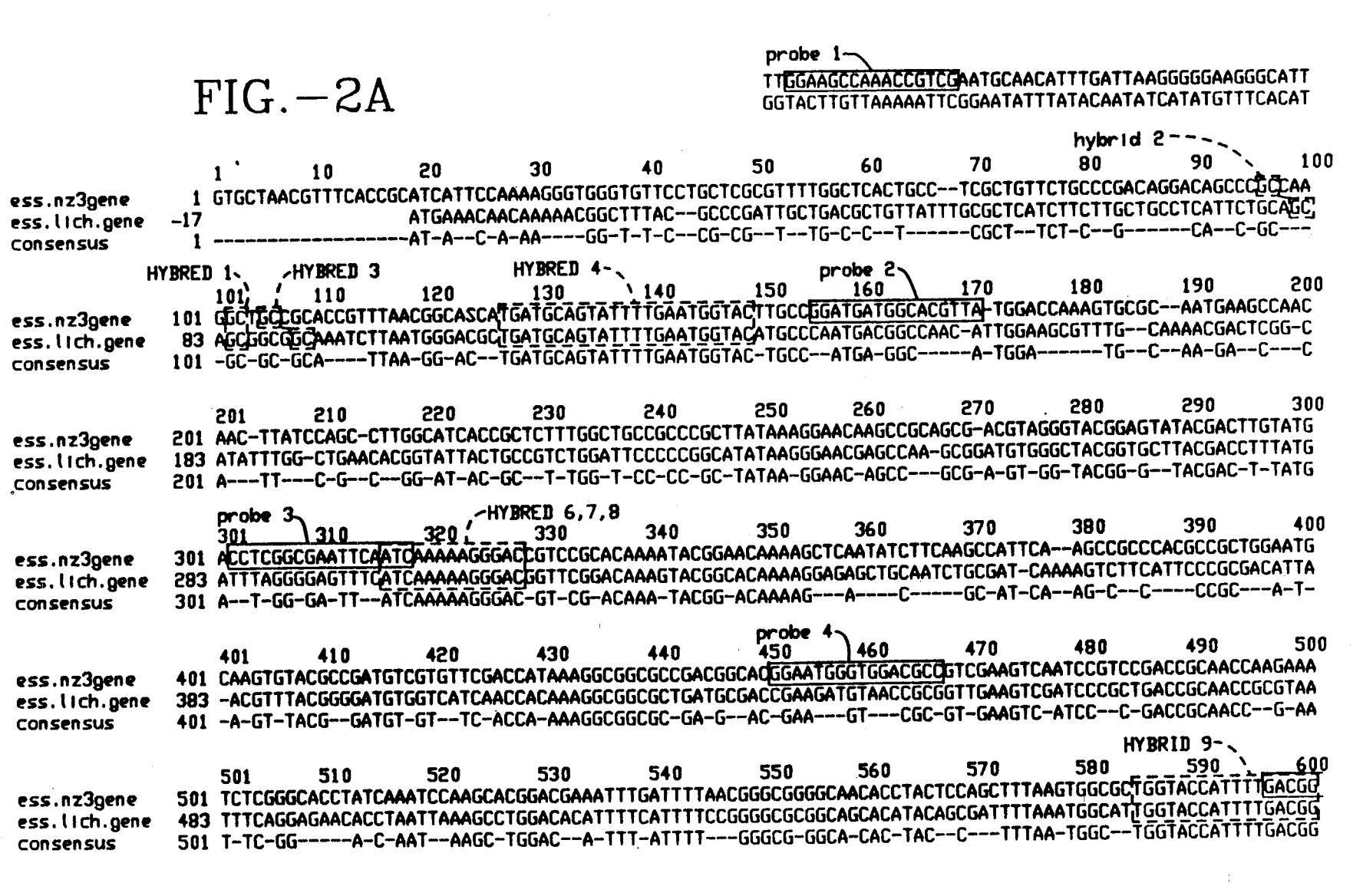

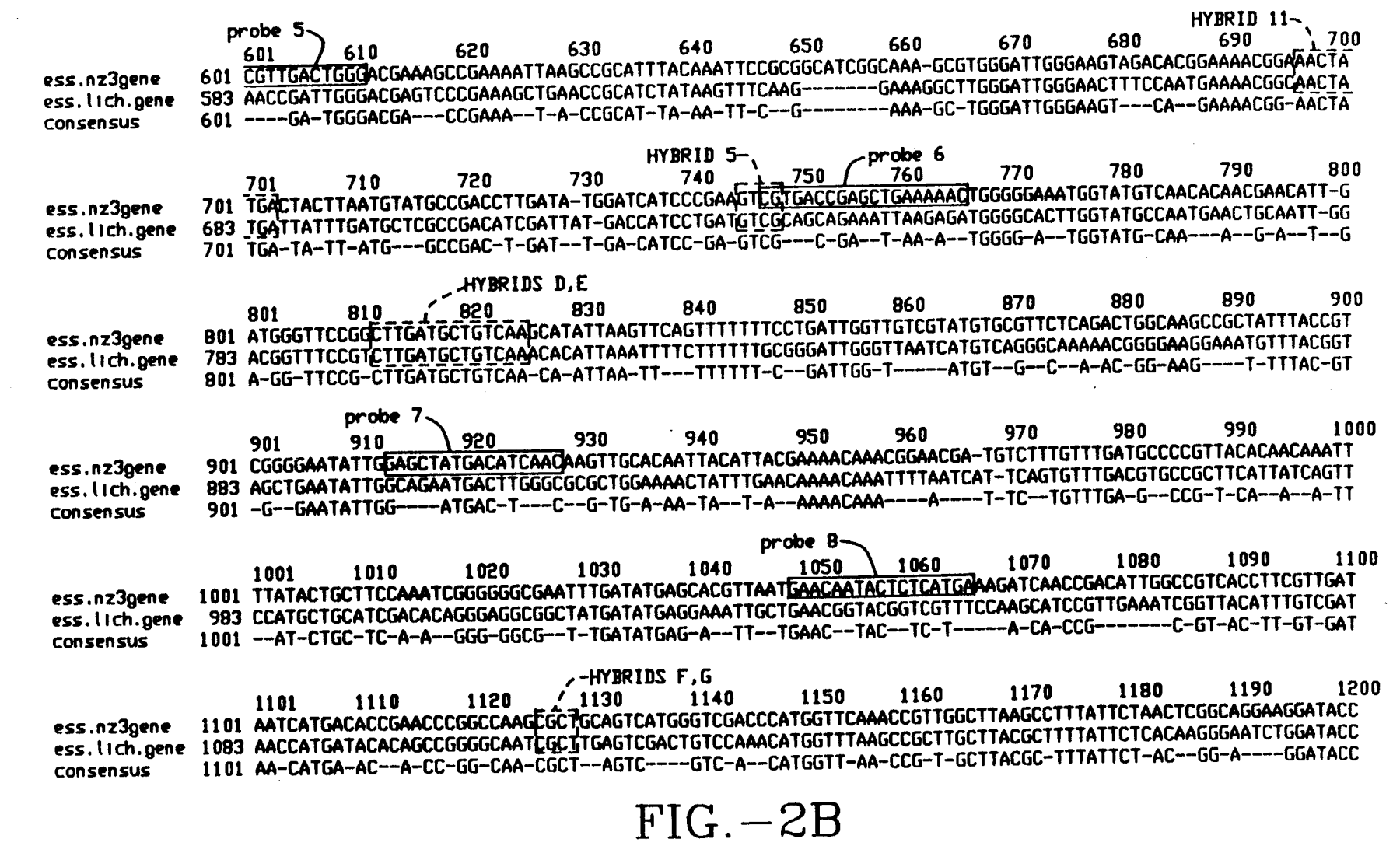

```
                         1210      1220      1230      1240      1250      1260      1270      1280      1290      1300
           probe 9
ess.nz3gene    1201 CGTGGGTCTTTTATGGTGACTAT-TATGGCATTCC----ACAAT-ATAAC------ATTCCTTCAC-TGAAAAGCAAAATCGATCCGCTCCTCATCGGCGC
ess.lich.gene  1183 CTCAGGTTTTCTACGGGGAT-ATGTACGGACGAAAGGAGACTCCAGGCGCGAAATTCCTGCC-TTGAAACACAAAATTGAACCGATCTTAAAAGCGAGA
consensus      1201 C-----GT-TT-TA-GG-GA---AT-TA-GG-A--------A-A-T-----A-C------ATTCCT-C-----TGAAA--CAAAAT-GA-CCG-TC-T-A---GCG-G-

1310      1320      1330      1340      1350      1360      1370      1380      1390      1400
ess.nz3gene    1301 AGGGATTATGCTTATGGAACGCAACATGATTATCTTGATCACTCCGACATCATCGGGTGGACAAGGGAAGGCGTTACCGAAAAACCAGGATCCGGACTGG
ess.lich.gene  1283 AAACAGTATGCTACGGAGCACAGCATGATTATTTCGACCACCATGACATTGTCGGCTGGACAAGGGAAGGGAGGCACGTTCGGTTGCAAATTCAGGTTGG
consensus      1301 A----A-TATGC-TA-GGA-C-CA-CATGATTAT-T-GA-CAC---GACAT--TCGG-TGGACAAGGGAAGGC---AC------CA---TC-GG-TGG 1410      1420      1430      1440      1450      1460      1470      1480      1490      1500
ess.nz3gene    1401 CCGCACTGATCACCGATGGGCGGGAGGAA-GCAAATGGAT-GTACGTTGGCAAACAACACGCGAAAAGTGTTCTATGACCTTACCGGCAACCGGAGT
ess.lich.gene  1383 CGGCATTAATAACAGACGGACCCGGTG----GGCAAAGCGAATGTATGTCGGCCGGCAAAACGCGTGAGACGATGGC--ATGACATTACCGGAAACCGTTCG
consensus      1401 C-GCA-T-AT-AC-GA-GG-CC-GG-G----GCAAA---GA--GTA-GT-GGC----CAA-ACGC--GA-A--TG----ATGAC-TTACGG-AACCG---

1510      1520      1530      1540      1550      1560      1570      1580      1590      1600
ess.nz3gene    1501 GACACCGTCACCATCAACAGTGATGATGGGGGAATTCAAAGTCAATGGCGGTTCGGTTCGGTTTGGGTTCCTAGAAAAACGACCGTCTCTACTATCG
ess.lich.gene  1483 GAGCCGGTTGTCATCAATTCGGAAAGGCTGGGAGAGTTTCACCGTAAACGGCGGGTCGGTTTCAATTTATGTTCAAAGATAG
consensus      1501 GA--C-GT----CATCAA-----GA-GG-TGGG-G----TTCA--GT-AA-GGCGG-TCGGTTC--TTT--GTTC--AGA-A-

1610      1620      1630      1640      1650      1660      1670      1680      1690      1700
ess.nz3gene    1601 CTTGGCCGATCACAACCCGACCGTTGGACCGAACCACGGTTGGTGGCATGGCCTTGA
consensus      1601 --------------------------------------------
```

NZ3 is B. stearothermophilus lich is B. licheniformis

```
PROTEIN
HOMOLOGY = 542
                                                              HYBRID 4
                      1         10        20        30        40       50
epl.nz3         1   VLTFHRII-RKGWVFLLAFWLTASLFCPTGQPAKAAAPFNGTMMQYFEWY
epl.b.lich     12   M-KQQKR-LYARLLTLLFALIFLLPHSAAAAANL--NGTLMQYFEWY
consensus       1   --------R------LL--------P------A---NGT-MQYFEWY 60        70        80        90       100
epl.nz3        51   LPDDGTLWTKVANEANNLSSLGITALWLPPAYKGTSRSDVGYGVYDLYDL
epl.b.lich     48   MPNDGQHWKRLQNDSAYLAEHGITAVWIPPAYKGTSQADVGYGAYDLYDL
consensus      51   -P-DG--W---N---L---GITA-W-PPAYKGTS--DVGYG-YDLYDL HYBRID 6
                             110       120       130       140      150
epl.nz3       101   GEFNQKGTVRTKYGTKAQYLQAIQAAHAAGMQVYADVVFDHKGGADGTEW
epl.b.lich     98   GEFHDKGTVRTKYGTKGELQSAIKSLHSRDINVYGDVVINHKGGADATED
consensus     101   GEF-QKGTVRTKYGTK-----AI----H-----VY-DVV--HKGGAD-TE- 160       170       180       190      200
epl.nz3       151   VDAVEVNPSDRNQEISGTYQIQAWTKFDFNGRGNTYSSFKWRWYHFDGVD
epl.b.lich    148   VTAVEVDPADRNRVISGEHLIKAWTHFHFPGRGSTYSDFKWHWYHFDGTD
consensus     151   V-AVEV-P-DRN--ISG---I-AWT-F-F-GRG-TYS-FKW-WYHFDG-D 210       220       230       240      250
epl.nz3       201   WDESRKLSRIYKFRGIGKAWDEVDTENGNYDYLMYADLDMDHPEVVTEL
epl.b.lich    198   WDESRKLNRIYKFQGK--AWDWEVSNENGNYDYLMLADIDYDHPDVAAEI
consensus     201   WDESRKL-RIYKF-G---AWDWEV--ENGNYDYLM-AD-D-DHP-V--E-

HYBRID D
                            260       270       280       290      300
epl.nz3       251   KNWGKWYVNTTNIDGFRLDAVKHIKFSFFPDWLSYVRSQTGKPLFTVGEY
epl.b.lich    248   KRWGTWYANELQLDGFRLDGFRLDAVKHIKFSFLRDWVNHVRAKTGKEMFTVAEY
consensus     251   K-WG-WY-N----DGFRLDAVKHIKFSF--DW---VR--TGK--FTV-EY
```

FIG.—6A

```
              301         310         320         330         340         350
epl.nz3    301 WSYDINKLHNYITKINGTMSLFDAPLHNKFYTASKSGGAFDMSTLMNNTL
epl.b.lich 298 WQNDLGALENYLNKTNFNHSVFDVPLHYQFHAASTQGGGYDMRKLLNGTV
consensus  301 W--D---L-NY--KTN----S-FD-PLH-F--AS--GG--DM--L-N-T-

351         360         370         380         390         400
epl.nz3    351 MKDQPTLAVTFVDNHDTEPGQALQSWVDPWFKPLAYAFILTRQEGYPCVF
epl.b.lich 348 VFKHPLKSVTFVDNHDTQPGQSLESTVQTWFKPLAYAFILTRESGYPQVF
consensus  351 ----P---VTFVDNHDT-PGQ-L-S-V--WFKPLAYAFILTR--GYP-VF 401         410         420         430         440         450
epl.nz3    401 YGDYYGIPQY---NIPSLKSKIDPLLIARRDYAYGTQHDYLDHSDIIGWT
epl.b.lich 398 YGDMYGTKGDSQREIPALKHKIEPILKARKQYAYGAQHDYFDHHDIVGWT
consensus  401 YGD-YG-------IP-LK-KI-P-L-AR--YAYG-QHDY-DH-DI-GWT 451         460         470         480         490         500
epl.nz3    451 REGVTEKPGSGLAALITDGPGGSKWMYVGKQHAGKVFYDLTGNRSDTVTI
epl.b.lich 448 REGDTSVANSGLAALITDGPGGQSECMSAGKTRET-WHDITGNRSEPVVI
consensus  451 REG-T----SGLAALITDGPGG-----------------D-TGNRS--V-I 501         510         520         530         540         550
epl.nz3    501 NSQGWGEFKVNGGSVSVWVPRKTTVSTIAWPITTRPWTGEFVRWTEPRLV
epl.b.lich 498 NSEGWESFTVNGGSVSIYVQR
consensus  501 NS-GW--F-VNGGSVS---V-R 551         560         570         580         590         600
epl.nz3    551 AWP
consensus  551 ---

CROSSOVER LOCI IN PROTEINS ENCODED BY ALPHA AMYLASE
GENES OF HYBRIDS 4, 6, AND D (BOXED)

FIG.—6B nz3 is B. stearothermophilus
lich is B. licheniformis
```

5,093,257

HYBRID PROKARYOTIC POLYPEPTIDES PRODUCED BY IN VIVO HOMOLOGOUS RECOMBINATION

This is a continuation of application Ser. No. 752,267 filed July 3, 1985, now abandoned.

FIELD OF THE INVENTION

The present invention is directed to hybrid polypeptides and processes for making the same. More particularly, the invention provides processes for producing hybrid DNA sequences which can express hybrid polypeptides having novel polypeptide sequences and novel physical properties.

BACKGROUND OF THE INVENTION

Advances in the field of recombinant DNA technology have resulted in the cloning of various naturally occurring DNA sequences and the expression of the underlying recombinant DNA to produce biologically active recombinant polypeptides. For example, human growth hormone has been produced in *E. coli* by fusing the coating sequences for this protein to an *E. coli* promoter (1). In a second example, tissue plasminogen activity, another rare human protein, has also been produced in *E. coli* (2).

Modifications of certain recombinant polypeptides have been made to investigate the properties of such modified polypeptides. To this end, naturally occurring DNA sequences have been cloned and modified by deleting or replacing amino acid residues of the naturally occurring polypeptide to modify the physical properties of the recombinant polypeptide, as for example, by site directed mutagenesis as disclosed in U.S. Pat. No. 4,518,584.

Recombinant polypeptides have also been modified by fusing recombinant DNA sequences. For example, the signal sequence from a plasmid-derived beta-lactamase was positioned at the amino-terminus of proinsulin through a common restriction site to facilitate the secretion of proinsulin (3).

Two different human alpha interferon DNA sequences have been combined by way of a common restriction site to form a DNA sequence containing sequences from alpha-1 interferon and alpha-2 interferon as described by Weissman (4). The alpha interferons expressed by such fused alpha interferon DNA sequence, however, demonstrated limited biological activity.

A major limitation in producing modified polypeptides by combining the underlying DNA at a restriction site, at more than one restriction site by way of a bridging synthetic oligonucleotide or by combining synthetic oligonucleotides to form the entire modified DNA sequence lies in the enormous amount of work which is required to produce a particular modified recombinant polypeptide. For example, such modifications require knowledge of the DNA and/or polypeptide sequence which if not available must be determined. Moreover, even if such sequences are known, the task of producing a modified polypeptide is far from simple and may result in a biologically inactive molecule.

Weber, et al., (5) disclose a method for making modified genes by in vivo recombination between DNA sequences encoding an alpha-1 and an alpha-2 human interferon sequence. A linear DNA sequence containing a plasmid vector flanked by the alpha-2 interferon gene on the 5' end and a portion of alpha-1 interferon gene on the 3' end was used to transfect a rec A positive strain of *E. coli*. Circularization of the linear plasmid by in vivo recombination between the partially homologous interferon gene sequences produced a number of modified interferon genes containing various portions of the alpha-1 and alpha-2 interferon gene sequences. Weber reports that some of these modified alpha interferon genes expressed modified alpha interferons having biological activity similar to unmodified alpha-2 interferons.

The efficiency of producing modified genes and polypeptides by in vivo circularization (recombination) of linear plasmids, as disclosed by Weber (5), is limited by the relative inefficiency of linear plasmids to transfect microorganisms as compared to circular plasmids. In addition, the two different but related genes on such linear plasmids are always separated by a replicable plasmid sequence. Circularization requires that the ends of the vector containing the two genes overlap to bring the two genes into close proximity with each other. The efficiency of recombination may therefore be limited by the linearity of such plasmid constructions.

Accordingly, it is an object herein to provide circular vectors containing replicable DNA sequences and DNA sequences encoding at least two different parental polypeptides and recombined circular vectors containing said replicable DNA sequences and a hybrid DNA sequence encoding a hybrid polypeptide corresponding to part of each parental polypeptide.

It is a further object of the present invention to provide efficient processes for making such recombined circular vectors and hybrid polypeptides.

Further, an object of the invention is to provide additional processes for isolating such recombined circular vectors.

Further, an object of the present invention is to provide biologically active hybrid polypeptides containing segments of polypeptide sequences derived from at least two parental polypeptides.

Still further, an object of the present invention is to provide biologically active hybrid enzymes such as hybrid amylases and hybrid proteases.

SUMMARY OF THE INVENTION

Novel circular vectors containing a replicable DNA sequence and parental DNA sequences encoding all or part of at least two distinct parental polypeptides are disclosed. Such vectors are used in novel processes to produce recombined circular vectors containing said replicable DNA sequences and hybrid DNA sequences comprising: (1) a first DNA sequence encoding the amino-terminal portion of a hybrid polypeptide corresponding to a first part of a first parental polypeptide sequence and (2) a second DNA sequence encoding a carboxy-terminal portion of said hybrid polypeptide corresponding to a first part of a second parental polypeptide sequence.

First and second parental DNA sequences encoding all or part of a first and second parental polypeptide sequence are ligated with a replicable DNA sequence to form a circular vector wherein said parental DNA sequences are in proximity with each other. Rec positive microorganisms are transformed with the thus formed circular vector to form a cell population containing a multiplicity of said circular vector wherein crossover recombination of at least one of said circular vectors is mediated by the naturally occurring recombination mechanism of the rec positive microorganism. Such crossover recombination of the vector excises a third DNA sequence which encodes a second part of each of said first and second parental polypeptide sequences to form a recombined circular vector comprising said replicable DNA sequences and said hybrid DNA sequences which encode a first part of each of said first and second parental polypeptide sequences. Such recombined vectors may be capable of expressing novel hybrid polypeptides or may be further modified to allow such expression.

A variation of the above described process utilizes a unique restriction site which is contained within said third DNA sequence. Excision of the third DNA sequence produces a recombined circular vector which no longer contains the unique restriction site. Treatment of isolated circular vector and recombined circular vector with an endonuclease specific for said unique restriction site produces linearized vector and circular recombined vector. The circular recombined vector is isolated from linearized vector by exposing a microorganism to such vectors to transform the microorganism with the recombined circular vector.

A process is also disclosed wherein said third DNA sequence comprises a DNA sequence which prevents expression of the second DNA sequence. Such sequences are typically transcription termination sequences. A functional promoter sequence is operably linked to said first DNA sequence. When the third DNA sequence is excised by a rec positive microorganism hybrid polypeptide is expressed. Such expression can be used to identify transformants which contain recombined vector.

This latter process can be further modified by positioning a fourth DNA sequence three prime to said second DNA sequence. This fourth DNA sequence encodes a defined selection characteristic, such as tetracycline resistance, which may be used to isolate transformants containing recombined vector which express the defined selection characteristics as a result of the excision of said third DNA sequence.

BRIEF DESCRIPTION OF THE DRAWINGS

FIG. 6 depicts the amino acid sequence for the alpha amylases derived from *B. stearothermophilus* and *B. licheniformis* and the consensus amino acid sequence between each.

DETAILED DESCRIPTION

Figure 1:
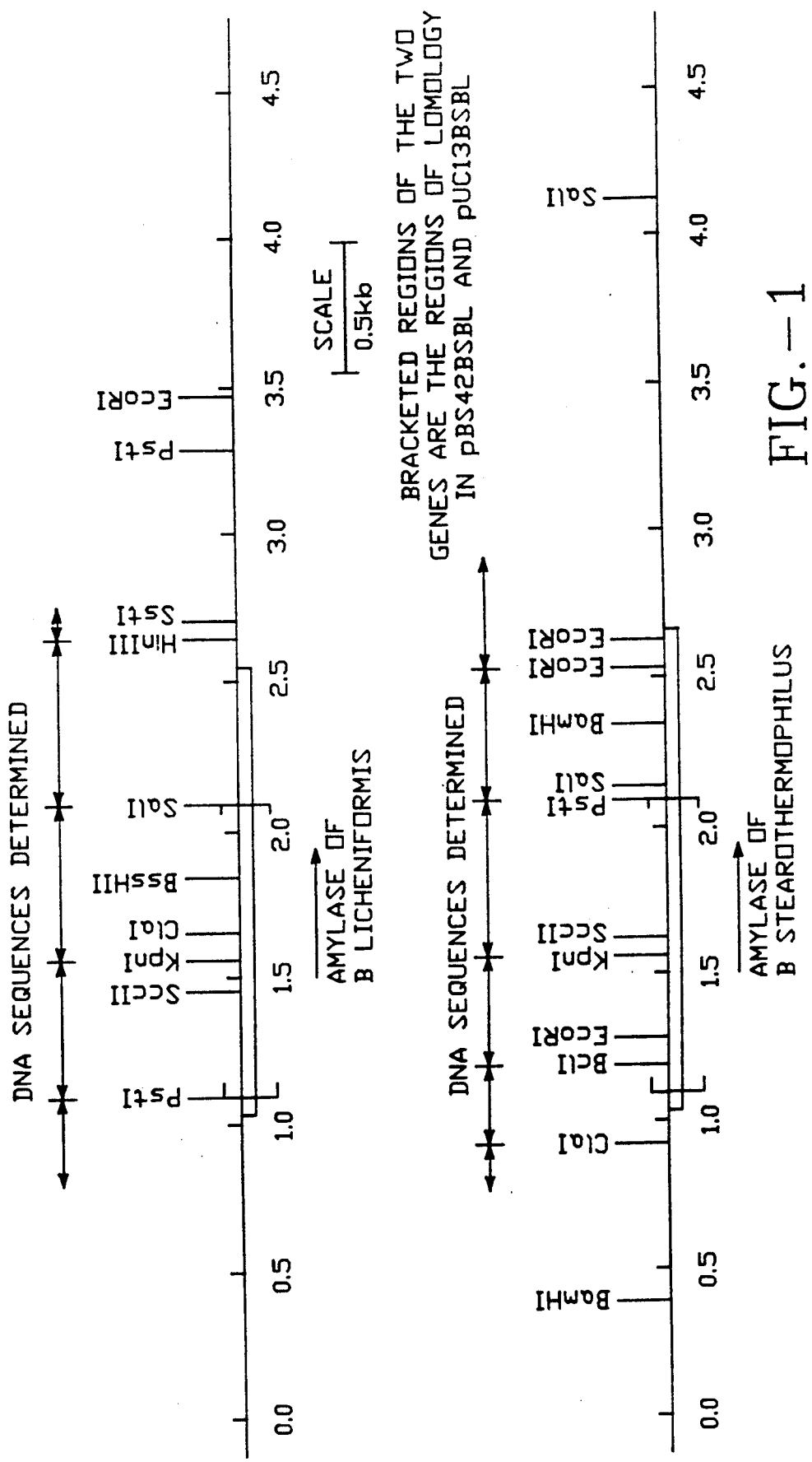
FIG. 1 depicts a partial restriction map of the alpha amylase DNA sequences derived from *B. licheniformis* and *B. stearothermophilus*.

Applicants have demonstrated that novel hybrid polypeptides having unique biological activity can be produced by homologous crossover recombination of DNA sequences contained on a circular vector. Parental DNA sequences encoding all or part of at least two different polypeptides are ligated with a replicable DNA sequence to form a circular vector. The parental DNA sequences may be joined in a tandem relationship whereby said sequences are in very close proximity or may be inserted at various positions within the circular vector to vary their proximity. Such variation in proximity may be useful in controlling the efficiency of recombination or may impose physical restraints which limit the regions in such parental DNA sequences wherein recombination may occur. Rec positive microorganisms transformed with the thus ligated circular vector were believed to initiate crossover recombination in regions of sequence homology between the parental DNA sequences. Recombined circular vectors were formed containing hybrid DNA sequences containing various portions of each parental DNA sequence. The point of actual crossover did not necessarily correspond to those regions of the parental DNA sequences which were homologous, such homology only being necessary to initiate crossover recombination. These hybrid DNA sequences encoded biologically active polypeptides which contained various amino-terminal and carboxy-terminal portions derived from each of the parental polypeptides.

As used herein, a "hybrid polypeptide" refers to recombinant polypeptides having an amino acid sequence which is a combination of partial sequences derived from at least two parental amino acid sequences. In some of the various preferred embodiments disclosed, hybrid polypeptides contained a variable amount of the amino-terminal peptide sequence derived from a specific *B. stearothermophilus* alpha amylase and a carboxy-terminal peptide sequence derived from a specific *B. licheniformis* alpha amylase. Other embodiments disclose hybrid polypeptides containing variable amounts of amino-terminal sequences derived from a specific *B. subtilis* alkaline protease and carboxy-terminal amino acid sequences from a specific *B. amyloliquefaciens* alkaline protease.

These specific embodiments are presented by way of example and are not intended to limit the scope of the present invention. In particular, alpha amylases or alkaline proteases from sources other than those specifically disclosed may be employed in practicing the present invention. Such parental polypeptides include for example alpha amylases derived from *B. coagulans* (e.g., ATCC 7050), *B. amyloliquefaciens* (e.g., ATCC 23842), *B. megaterium* (e.g., ATCC 6458), *B. alcalophilus* (e.g., ATCC 21591), and *B. cereus* (e.g. ATCC 21768). Examples of other alkaline proteases include those derived from *B. licheniformis* (e.g. ATCC 21415), *B. alcalophilus* (e.g., ATCC 21522) and *B. cereus* (e.g. ATCC 21768).

In general, the present invention may also be used to generate hybrid polypeptides by combining amino acid sequences from related or unrelated polypeptides. Hybrid polypeptides containing related amino acid sequences may exhibit unique physical properties whereas hybrids of unrelated polypeptides may produce a bifunctional hybrid polypeptide. The only limitation in choosing parental polypeptides is functional. The underlying DNA sequences encoding each of the parental polypeptides must have sufficient sequence homology to permit in vivo recombination.

Examples of various parental polypeptides which may be combined according to the present invention include plasminogen activators, growth hormones, interferons, lymphotoxins, aspartyl proteases, *B. thuringiensis* toxins, celluloses, and glucoamylases.

A "hybrid DNA sequence" is a DNA sequence encoding the above described hybrid polypeptides. In some disclosed embodiments such hybrid DNA sequences further include a functional promoter operably linked to said hybrid DNA sequence whereby the hybrid polypeptide encoded by the underlying hybrid DNA can be expressed. Such promoters may be the native promoter of a parent DNA sequence or may be derived from sources known to those skilled in the art and functionally inserted by well known methods to effect expression of hybrid polypeptide. In some embodiments a promoter sequence is not required to produce a hybrid DNA sequence. A promoter sequence may be introduced into such recombined vectors after recombination to enable expression of the hybrid DNA sequence.

A "parental DNA sequence" refers to a DNA sequence encoding all or part of a particular polypeptide sequence. As disclosed herein, a first part from at least two parental DNA sequences are recombined in vivo to form a hybrid DNA sequence encoding a hybrid polypeptide. Depending on the particular embodiment, a second part of each parental DNA sequence is excised during formation of said hybrid DNA sequence.

A "rec positive microorganism" refers to genotypes of prokaryotic and eukaryotic microorganisms which are capable of recombination and in particular are capable of mediating recombination of the circular vector of the present invention. Such microorganisms in general include prokaryotes such as Bacillus, *E. coli* and other species of the Enterobacteriaciae bacteria, Pseudomonas, Corynebacteria, Lactobacilli, Streptomyces, and Agrobacterium, and eukaryotes such as *Saccharomyces cerevisiae* and other yeasts, Aspergillus and other filamentous fungi, and tissue culture cells from avian or mammalian origins.

The "replicable DNA sequences" which form a part of the circular vector and recombined vector of the present invention contain replication and control sequences which are derived from vector species which are compatible with the particular rec positive microorganism used to mediate in vivo recombination. Such replicable DNA sequences ordinarily carry a replication site as well as sequences which encode proteins that are capable of providing phenotypic selection in transformed cells. For example, when a rec positive *E. coli* is chosen for in vivo recombination, DNA sequences derived from pBS42(17) (ATCC #37279), pBR322(25) (ATCC #37017), pUC series plasmid (26), and RSF1010(44) may be used. When a rec positive eukaryote such as Saccharomyces, Aspergillus, or mammalian tissue culture cells is used replicable DNA sequences may be derived respectively from the yeast 2-μ vector (35), the Aspergillus integration vector p3SR2(36) and SV40(37).

As used herein, a functional promoter operably linked to a coding DNA sequence refers to a promoter sequence which controls the transcription and translation of the coding sequence. The promoter sequence is chosen so that it is functional in the microorganism chosen for expression. For example promoter sequences (including ribosome binding sites) derived from Lambda $P_L$ (38), as well as the trp (39) or tac (40) promoters may be operably linked to coding sequences to express polypeptide in *E. coli*. When *B. subtilis* is the expression host the *B. subtilis* alkaline protease promoter (32) or alpha amylase promoter of *B. amyloliquefaciens* (41) may be used. Expression in yeast may be under the control of the promoter for the GAPDM of *S. cerevisiae* (42) while expression in filimentous fungi may be mediated by the promoter for B-glucosidase from *Aspergillus niger* (43). The early promoter of SV40(37) is preferred for expression in mammalian cells.

General Methods

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate. The various restriction enzymes used herein are commercially available and their reaction conditions, cofactors and other requirements as established by the enzyme suppliers were used. In general, about 1 microgram of plasmid or DNA fragment is used with about 1 unit of enzyme and about 20 microliters of buffer solution. Appropriate buffers and substrate amounts with particular restriction enzymes are specified by the manufacturer. Incubation times of about one hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme may be followed by bacterial alkaline phosphatase hydrolysis of the terminal 5' phosphates to prevent the two restriction cleaved ends of a DNA fragment from forming a closed loop that would impede insertion of another DNA fragment at the restriction site.

"Recovery" or "isolation" of a given fragment of DNA from a restriction digest means separation of the digest by a polyacrylamide gel electrophoresis, identification of the fragment of interest by comparison of its mobility versus that of marker DNA fragments of known molecular weight, removal of the gel section containing the desired fragment, and separation of the DNA from the gel generally by electroelution (6,7).

"Ligation" refers to the process of forming phosphodiester bonds between two double-stranded nucleic acid fragments (8). Unless otherwise stated, ligation was accomplished using known buffers in conditions with ten units of T4 DNA ligase ("ligase") per 0.5 microgram of approximately equal molar amounts of the DNA fragments to be ligated.

"Transformation" means introducing DNA in to an organism so that the DNA is replicable, either as an extrachromosomal element or chromosomal integrant. Unless otherwise stated, the method used herein for transformation of *E. coli* is the CaCl$_2$ method of Mandel (9) and for Bacillus, the method of Anagnostopolous (10).

"Oligonucleotides" are short length single or double stranded polydeoxynucleotides which were chemically synthesized by the method of Crea et al., (11) and then purified on poly-acrylamide gels.

"Preparation" of DNA from transformants means isolating plasmid DNA from microbial culture. Unless otherwise provided the alkaline/SDS method was used (12).

The following specific examples are intended to illustrate more fully the nature of the present invention without acting as a limitation upon its scope.

EXAMPLES OF PREFERRED EMBODIMENTS

In one example of a preferred embodiment, *B. stearothermophilus* alpha amylase DNA sequences containing the native promoter for *B. stearothermophilus* alpha amylase operably linked to the entire DNA sequence encoding *B. stearothermophilus* alpha amylase was cloned and isolated. The DNA sequence encoding the alpha amylase of *B. licheniformis* was similarly cloned.

A PstI restriction site near the 5' end of the structural DNA sequence encoding *B. licheniformis* alpha amylase and a PstI restriction site near the 3' end of the structural DNA sequence encoding *B. stearothermophilus* alpha amylase were used to ligate DNA sequences encoding each of the parental amylases in a tandem arrangement on a circular vector.

Homologous crossover recombination between the alpha amylase DNA sequence was mediated by a rec positive microorganism to form hybrid DNA sequences encoding a number of hybrid amylases derived from *B. licheniformis* and *B. stearothermophilus*. Transformants containing such hybrid DNA sequences were identified by detecting hybrid alpha amylase activity.

In an example of another embodiment, a vector which had not undergone homologous crossover recombination was linearized by digestion with PstI. Vectors which had recombined to form hybrid DNA sequence encoding hybrid alpha amylases no longer contained the PstI site used to join the two alpha amylase DNA sequences. Since such a PstI site was unique in the vectors constructed, recombined vectors resisted linearization. Such non-linearized recombined vector were isolated from linearized vector by transformation of a second microorganism.

In both embodiments crossover recombination initiated at homologous sequences of the *B. stearothermophilus* and *B. licheniformis* alpha amylase encoding DNA sequences formed mutant vectors containing hybrid DNA sequences encoding the promoter of *B. stearothermophilus* alpha amylase, various portions of the amino-terminal sequence of *B. stearothermophilus* alpha amylase and various portions of the carboxy-terminal sequence of *B. licheniformis* alpha amylase. The various hybrid alpha amylases expressed by such hybrid DNA sequences demonstrated unique properties as compared to the parental alpha amylases from *B. stearothermophilus* and *B. licheniformis*. Other examples of preferred embodiments are also disclosed.

EXAMPLE 1

A. Cloning of the alpha amylase genes of *Bacillus licheniformis* and *Bacillus stearothermophilus*.

*B. licheniformis* or *B. stearothermophilus* DNA was partially digested with Sau3A and DNA fragments larger than 6 kb (kilobases) were separated on sucrose gradients. The *B. licheniformis* strain used as a source of genomic DNA was strain MCIB 8061 obtained from the National Collection of Industrial Bacteria, Torrey Research Station, Aberdeen, Scotland. The *B. stearothermophilus* strain used as a source of genomic DNA was strain NZ-3 which has been deposited by Assignee in the American Type Culture Collection under accession number 39536. The bacteriophage lambda vector λ1059 (13) was completely digested with BamHI and treated with calf intestinal phosphatase to minimize self-ligation. 500 ng of vector and 500 ng of bacterial DNA fragments were ligated in a 20 ul reaction volume using T4 DNA ligase. The DNA contained in the reaction was packaged in vitro using a commercial (Promega Biotec) (Madison, WI) packaging extract (14) and then used to infect *E. coli* Q358 (15) (6) and Q359, (a P2 lysogen of Q358) (15). The number of recombinant plaques was approximately $2.5 \times 10^3$ in typical reactions.

Approximately $5 \times 10^3$ plaques were plated onto *E. coli* Q359 bacteria on LB plates containing 0.5% starch to screen for alpha amylase activity. These plates were exposed to iodine vapors to stain the starch (16). Five plaques which were surrounded by clear halos were found in the *B. licheniformis* library. Three such plaques were found in the *B. stearothermophilus* library. DNA was prepared from each one of the amylase positive *B. licheniformis* phage (designated λ-amy-BL) and the *B. stearothermophilus* phage (designated λ-amy-BS).

Figure 3:
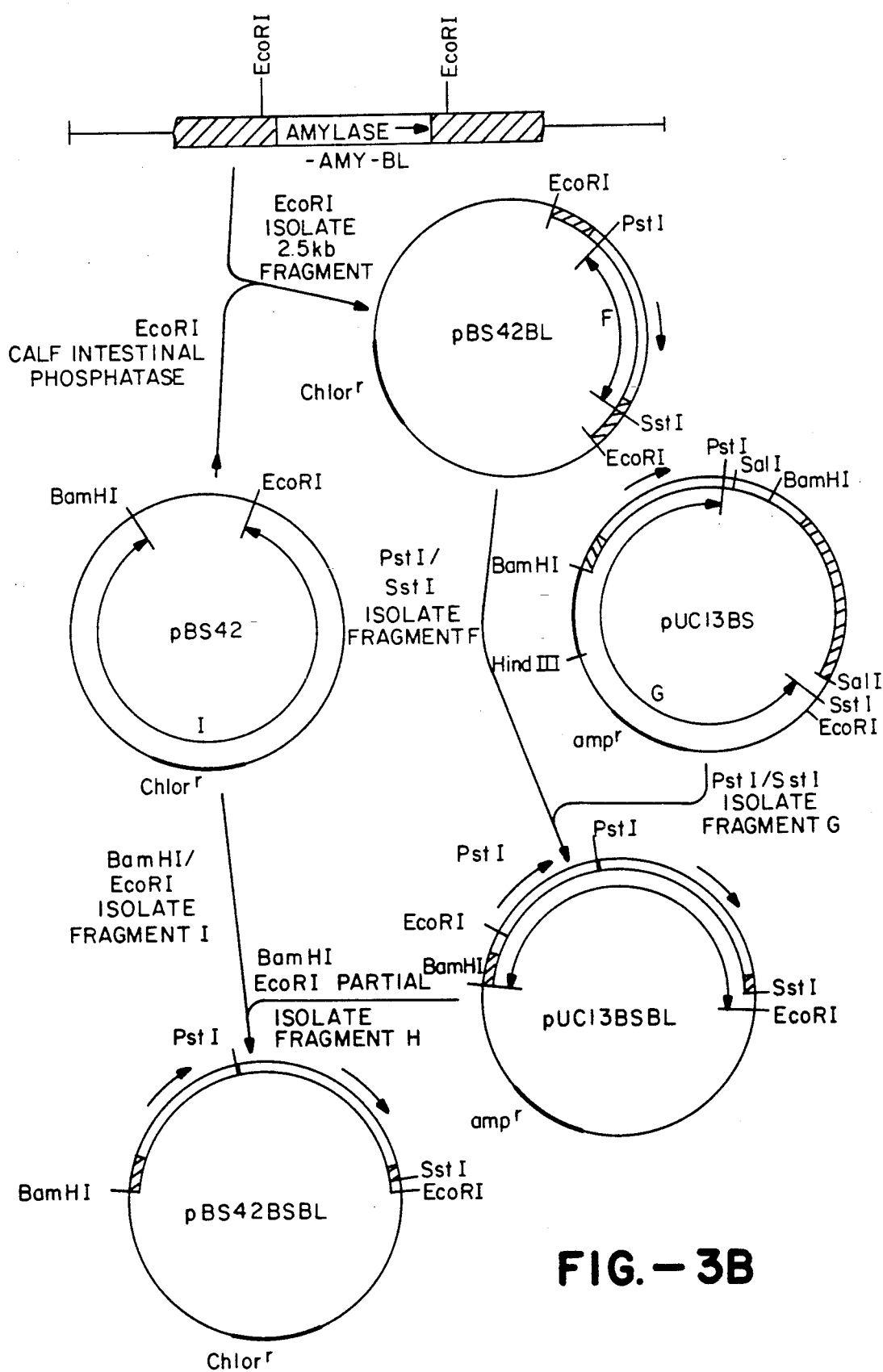
FIG. 3a depicts the construction of a plasmid containing DNA sequences encoding the alpha amylase of *B. stearothermophilus*.
FIG. 3b depicts the construction of a plasmid containing a tandem arrangement of DNA sequences encoding a portion of *B. stearothermophilus* alpha amylase and a portion of *B. licheniformis* alpha amylase.

Referring now to FIG. 3B, the *E. coli* -*B. subtilis* shuttle vector pBS42 (17), ATCC 37279, was cleaved with BamHI or EcoRI and treated with calf intestinal alkaline phosphatase to minimize self ligation. This cleaved shuttle vector was ligated with DNA from λ-amy-BL which had also been digested with BamHI or EcoRI respectively. Transformation of *E. coli* 294, (18), ATCC No. 31446, gave rise to numerous chloramphenicol resistant transformants, many of which showed clear halos when stained with iodine vapors. Digestion of each one of the amylase positive (amy+) BamHI and EcoRI subclones revealed inserted fragments of 9.4 kb and 3.2 kb respectively. These results show that the alpha amylase gene of *B. licheniformis* was contained entirely within either of these fragments. The EcoRI subclone was designated pBS42-BL and is shown in FIG. 3B.

Figure 2:
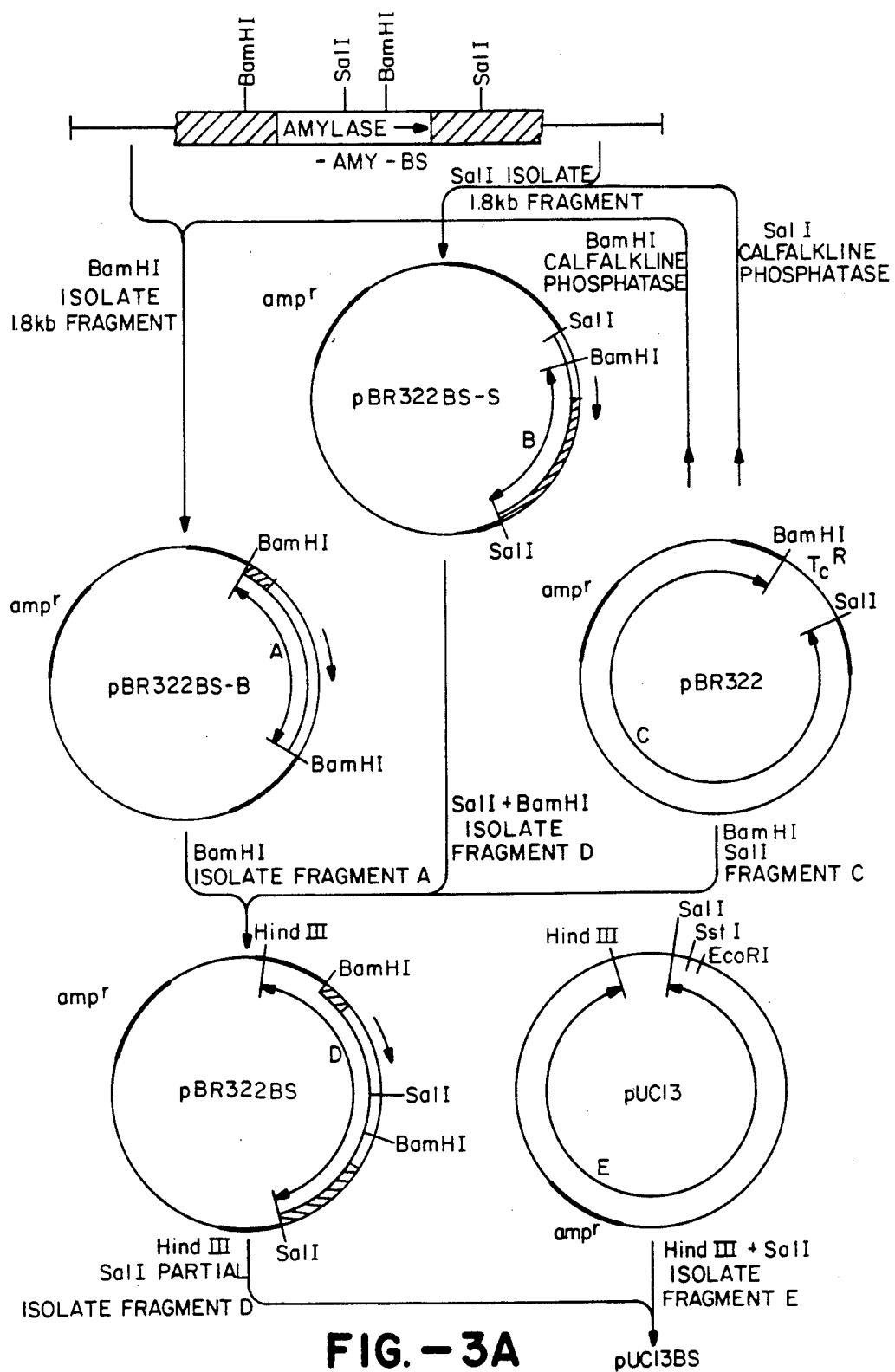
FIGS. 2A and 2B depict the nucleotide sequence for the alpha amylases derived from *B. stearothermophilus* and *B. licheniformis* and the consensus sequence between each.

The plasmid pBS42-BL was subjected to further digestions with various restriction enzymes in order to generate the restriction map depicted in FIG. 1. Various subfragments of the inserted DNA were subcloned into M13 sequencing vectors (19) in order to determine preliminary DNA sequence information by the dideoxy chain termination method (21). Sequences near the unique KpnI site were found to be highly homologous to those of the alpha amylase gene of *B. amyloliquefaciens*. By making the assumption that the *B. licheniformis* amylase gene was structurally similar to the *B. amyloliquefaciens* gene (41) the appropriate fragments to sequence in detail were easily chosen. FIG. 1 shows the regions that were completely sequenced. An open reading frame of 1536 bp was found which had a high degree of homology to the entire alpha amylase gene of *B. amyloliquefaciens*. The DNA sequence of *B. licheniformis* alpha amylase is shown in FIGS. 2A and 2B.

DNA from λ-amy-BS was digested with various restriction enzymes, separated on a 1% agarose gel, transferred to a nitrocellulose filter (21), and subjected to DNA-DNA hybridization (22). The probe used was the PstI-SstI fragment containing most of the coding sequences of the *B. licheniformis* amylase gene (FIG. 1). This fragment was radioactively labeled with γ-$^{32}$P using the nick translation method (23). Hybridization was performed under standard high stringency conditions (24). A BamHI fragment of 1.8 kb and a Sal I fragment of 1.8 kb were among the positively hybridizing fragments. Both of these fragments were subcloned into pBR322, and cleaved with BamHI or Sal I and ligated with BamHI or Sal I digested pBR322 to generate plasmids pBR322BS-B and pBR322BS-S as depicted in FIG. 3A. A detailed restriction map of the inserted fragments is shown in FIG. 1. This information was used to isolate a variety of subfragments for cloning into M13 sequencing vectors for preliminary DNA sequence analysis. Sequences near the unique KpnI site were found which were highly homologous to those of the alpha amylase genes of both *B. amyloliquefaciens* and *B. licheniformis*. Assuming that the structure of the *B. stearothermophilus* alpha amylase gene was similar to the other two it was possible to choose which other subfragments of the inserted fragments in pBR322BS-B and pBR322BS-S to sequence completely. The entire sequence of *B. stearothermophilus* alpha amylase is shown in FIGS. 2A and 2B. These studies revealed a 1581 bp open reading frame which was highly homologous to that of the other alpha amylase genes.

B. Construction of *B. stearothermophilus* alpha amylase plasmid vector pUC13BS and *B. stearothermophilus* -*B. licheniformis* alpha amylase precursor plasmids pUC13BSBL and pBS42BSBL.

As depicted in FIG. 3A, DNA from pBR322BS-B was digested with BamHI and a 1.8 kb fragment (fragment A) was isolated. Plasmid pBR322BS-S was doubly digested with BamHI and Sal I and a 1.8 kb fragment (fragment B) was isolated. Plasmid pBR322 was doubly digested with BamHI and Sal I and the larger vector fragment (fragment C) was isolated. Fragments A, B, and C were joined by ligation. The reaction was transformed into *E. coli* 294. One ampicillin resistant colony, containing plasmid pBR322BS was isolated. This plasmid was digested completely with HindIII and partially with Sal I and a 4.2 kb fragment (fragment D) was isolated. The vector pUC13 (26) was digested with with HindIII and Sal I and the larger vector fragment (fragment E) was isolated. Fragments D and E were joined by ligation and transformed into *E. coli* 294. An ampicillin resistant colony containing plasmid pUC13BS was isolated. This colony was found to produce a zone of clearing on an LB starch agar plate, and therefore was presumed to contain on its plasmid the entire gene of *B. stearothermophilus* alpha amylase.

Referring now to FIG. 3B, the *B. licheniformis* alpha amylase plasmid pBS42BL was cleaved with SstI and PstI and the smaller fragment (fragment F) was isolated. The *B. stearothermophilus* plasmid pUC13BS was also cleaved with SstI and PstI and the larger vector fragment (fragment G) was isolated. Fragments F and G were joined by ligation and then used to transform *E. coli* 294. One ampicillin resistant colony containing plasmid pUC13BSBL was selected. This colony did not produce an active alpha amylase as determined by its failure to produce a halo of clearing on an LB starch agar plate. This result was expected because pUC13BSBL lacks the carboxy-terminal codons of the *B. stearothermophilus* alpha amylase gene and also the amino-terminal codons of the *B. licheniformis* alpha amylase gene. In addition the codons of the latter gene are not in the same reading frame as those of the former gene. The plasmid pUC13BSBL was cleaved completely with BamHI and partially digested with EcoRI. Fragment H was isolated. The *E. coli* -*B. subtilis* shuttle vector pBS42 was digested with BamHI and EcoRI and the larger vector fragment (fragment I) was isolated. Fragments H and I were joined by ligation and transformed into *E. coli* 294. One chloramphenicol resistant transformant, pBS42BSBL was saved. This colony produced no alpha amylase as determined by its failure to produce a halo of starch clearing on LB starch agar plates. This was expected because this plasmid contains the same alpha amylase sequences as pUC13BSBL.

C. The generation of hybrid alpha amylase DNA sequences and expression of their encoded hybrid proteins.

Ten ng of plasmid pBS42BSBL was used to transform *E. coli* 294 (rec A positive). The reaction was plated on LB-starch plates supplemented with 12.5 ug/ml chloramphenicol. About 3×10$^4$ colonies were obtained. Six of these produced halos due to starch hydrolysis. These colonies were presumed to contain plasmids in which the *B. stearothermophilus* and *B. licheniformis* alpha amylase DNA sequence within the plasmid had recombined by homologous recombination to give rise to hybrid DNA sequences encoding active hybrid alpha amylases. The region of homology (in which recombination was expected to occur) between the two alpha amylase gene fragments in pBS42BSBL is about 1.0 kb. These data would therefore indicate that the frequency for such recombination events was 6/3×10$^4$ or 2×10$^{-4}$.

EXAMPLE 2

In order to reduce the background of colonies containing pBS42BSBL a plasmid preparation from pBS42BSBL transformed *E. coli* 294 was digested with PstI prior to a second transformation. It was reasoned that in all cases in which recombination between the *B. stearothermophilus* and *B. licheniformis* gene fragments had occurred the PstI site (unique in the plasmid) would have been deleted. Thus such hybrid recombined plasmids would be resistant to PstI digestion, whereas unrecombined plasmids would be linearized by PstI digestion. The transformation efficiency of circular plasmids is two to three orders of magnitude greater than that for such linearized forms. It was therefore expected that the digestion of the pBS42BSBL with PstI prior to transformation would increase the ratio of colonies containing the recombined plasmids to those containing unrecombined plasmids. Thus 1000 ng of a PstI-treated plasmid preparation from pBS42BSBL transformed *E. coli* 294 was used to transform *E. coli* 294 a second time. 2032 colonies were obtained. 517 (approximately 25%) produced halos of starch hydrolysis on LB starch agar plates indicating the synthesis of active hybrid alpha amylase.

EXAMPLE 3 air dried and autoradiographed. The results are shown in Table 1.

TABLE 1

| | Signals with Oligonucleotide Probes | | | | | | | | | Crossover loci position in B. stearothermophilus |
|---|---|---|---|---|---|---|---|---|---|---|
| Hybrid | 1 | 2 | 3 | 4 | 5 | 6 | 7 | 8 | 9 | alpha amylase gene |
| 1 | + | − | − | − | − | − | − | − | − | 32 to 154 |
| 2 | + | − | − | − | − | − | − | − | − | 32 to 154 |
| 3 | + | − | − | − | − | − | − | − | − | 32 to 154 |
| 4 | + | − | − | − | − | − | − | − | − | 32 to 154 |
| 5 | + | + | + | + | + | − | − | − | − | 612 to 746 |
| 6 | + | + | + | − | − | − | − | − | − | 318 to 450 |
| 7 | + | + | + | − | − | − | − | − | − | 318 to 450 |
| 8 | + | + | + | − | − | − | − | − | − | 318 to 450 |
| 9 | + | + | + | + | − | − | − | − | − | 467 to 595 |
| D | + | + | + | + | + | + | − | − | − | 767 to 912 |
| E | + | + | + | + | + | + | − | − | − | 767 to 912 |
| 11 | + | + | + | + | + | − | − | − | − | 612 to 746 |
| F | + | + | + | + | + | + | + | + | − | 1067 to 1197 |
| G | + | + | + | + | + | + | + | + | − | 1067 to 1197 |
| pBS42BL | − | − | − | − | − | − | − | − | − | |
| pUC13BS | + | + | + | + | + | + | + | + | + | |
| pBS42BSBL | + | + | + | + | + | + | + | + | − | |

Numbers are nucleotide positions of B. stearothermophilus DNA sequence given in FIG. 2A and 2B. It was assumed that all positive signals were due to the presence of the entire sequence complimentary to the hybrizing probes.

A. Characterization of the hybrid DNA sequences contained in alpha amylase producing pBS42BSBL transformants of E. coli 294

The assumption was made that the amy+ colonies arose as a result of single crossover events within the pBS42BSBL plasmid between the B. stearothermophilus and B. licheniformis gene fragments in a region in which they have sequence homology. It was reasoned that such recombined genes would contain 5' sequences contributed by the B. stearothermophilus gene and 3' sequences contributed by the B. licheniformis gene. In order to verify this notion the following experiment was performed. Low homology regions of 16–18 nucleotides at intervals of about 150 bp were selected. Oligonucleotides, indicated as probes 1–9 in FIGS. 2A and 2B, corresponding to the sense strand of the B. stearothermophilus gene in these regions were synthesized (11). These oligonucleotides were endlabeled with $\gamma^{32}$P-ATP and T4 polynucleotide kinase in order to produce hybridization probes to detect B. stearothermophilus sequences. It was reasoned that all sequences 5' of the crossover locus would be derived from the B. stearothermophilus gene and would therefore hybridize to the corresponding (perfect homology) oligonucleotide probes. Sequences 3' of the crossover locus would be derived from the B. licheniformis gene and would therefore fail to hybridize to the corresponding (low homology) oligonucleotide probes under the conditions employed. Twelve amy+ colonies postulated to contain recombined hybrid alpha amylase DNA sequences as well as colonies containing pUC13BS, pBS42BL, and pBS42BSBL were selected for DNA-DNA hybridization with each of the oligonucleotide probes. All of these colonies were inoculated onto each of 9 nitrocellulose filter paper strips. These strips were placed on an LB agar plate. The plate was incubated overnight at 37° C. to allow colony growth. The filters were then prepared for hybridization by standard methods (27). In separate vessels the nine strips were incubated with each of the oligonucleotide probes using standard methods for low stringency hybridization. (2) The filters were washed in 2×SSC and 0.1% SDS at 37° C., then As expected the probes all hybridized to B. stearothermophilus sequences but not to B. licheniformis sequences. This is indicated by positive signals of hybridization with all probes to the DNA from cells containing pUC13BS which contains the entire B. stearothermophilus alpha amylase gene and negative hybridization signals to the DNA of cells containing pBS42BL which contains the entire B. licheniformis alpha amylase gene but no sequences from the B. stearothermophilus gene. The DNA from cells containing pBS42BSBL gave positive signals with all probes except probe 9 because probe 9 corresponds to a region of the B. stearothermophilus gene 3' of that present in this plasmid.

The 14 putative hybrids showed a variety of hybridization patterns. For example hybrids 1, 2, 3, and 4 hybridized to probe 1 but not to the other (more 3') probes 2–8. This indicated crossover between sequences corresponding to probes 1 and 2. In another example, hybrid 9 hybridized to probes 1–4 but not to the more 3' probes 5–9. This indicated a crossover between the sequences corresponding to probes 4 and 5. As shown in Table 1 other crossover regions were similarly identified in the remaining hybrids. In other experiments (not shown) hybrids with crossovers between any pair of probe regions were found although with highly variable frequencies, e.g. crossovers between probes 1 and 2 were very common (about 20%) whereas crossovers between probe regions 2 and 3 were quite rare (about 1%).

The above results indicate that the crossovers between the alpha amylase gene fragments were widely dispersed over the approximately 1.0 kb region of homology between the two genes. However, it was of interest to study this distribution in more detail. Thus we determined the DNA sequence of the hybrid genes in their crossover regions by direct sequencing of sodium hydroxide collapsed plasmids using the dideoxy chain termination method (28). For a given hybrid, synthesis was primed using the most 3' synthetic oligonucleotide which hybridized to the hybrid. In all cases the sequences determined clearly showed the crossover loci. The crossover loci for the twelve hybrids are shown in the stippled boxes of FIGS. 2A and 2B. For example, in hybrid 9 (FIG. 2A) the crossover occurred between bp 585 and bp 600, as indicated by the presence of sequences derived from the *B. stearothermophilus* gene 5' of this region and the sequences derived from the *B. licheniformis* gene 3' of this region.

B. Analysis of the hybrid alpha amylase enzymes produced by plasmid hybrids 4, 6, and D

*E. coli* 294 cells containing pBS42BL or plasmid hybrids 4, 6 or D were cultured overnight in shaker flasks (120 rpm) containing LB medium supplemented with 12.5 ug/ml chloramphenicol. *E. coli* 294 cells containing plasmid pUC13BS were similarly cultured except that 50 ug/ml of carbenicillin rather than chloramphenicol was added to the LB medium. Cells were collected by centrifugation and fractionated into cytoplasmic and periplasmic fractions by the osmotic shock method (29). These fractions were assayed for alpha amylase activity by the micro-Phaedabas assay (Pharmacia, Inc., Piscataway, N.J.) which measures starch hydrolosis. In all cases most of the activity (80-85%) was found to be associated with the periplasmic fraction. Thus this fraction was used for purification of the alpha amylases produced in the five cultures.

To purify the enzymes, the periplasmic fractions were poured over a column containing insoluble starch at 4° C. which resulted in the binding of the alpha amylases to the starch. The enzymes were then eluted from the column by raising the temperature to 50° C. Starch was removed from the enzymes by gel permeation chromatography on a P-2 column (Bio-Rad Laboratories, Richmond, Calif.) followed by DEAE chromatography (30). Each of the purified alpha amylases was pure as judged by its homogeneity on SDS-polyacrylamide gels. The protein concentration for each purified protein was determined by the dye binding method of Bradford (31).

Figure 5:
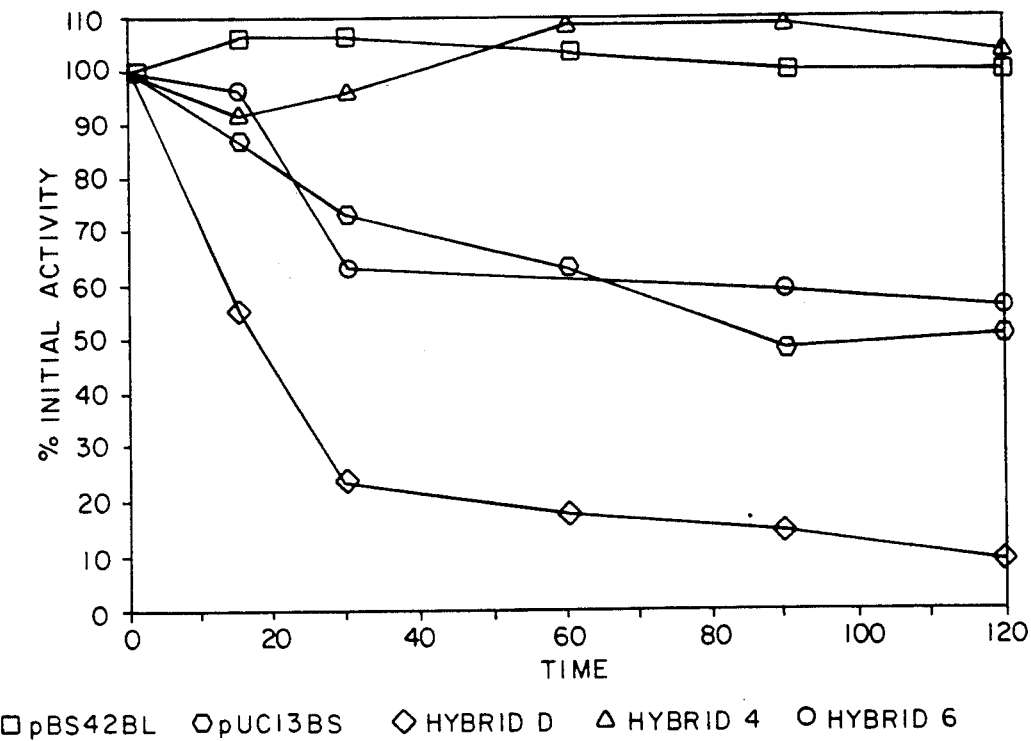
FIG. 5 depicts the thermal stability of various hybrid alpha amylases at 90° C. as a function of time.

The thermostabilities of the purified alpha amylases were determined as follows. Equal concentrations of the enzyme were incubated at 90° C. Aliquots were removed at various times and assayed for alpha amylase activity at 70° C. using the micro-Phaedabas assay. The results are shown in FIG. 5. The parental *B. licheniformis* enzyme produced from the pBS42BL plasmid retains essentially all of its activity even after prolonged incubation (120 min.) at 90° C., whereas the parental *B. stearothermophilus* enzyme produced from the plasmid pUC13BS loses about 50% of its activity under these conditions. The hybrid enzymes encoded by the hybrid DNA sequences of hybrids 4, 6, and D show a variety of thermostabilities. Hybrid 4 retains essentially all of its activity after incubation at 90° C. for 120 min. As shown in FIG. 6 this protein is structurally identical to the *B. licheniformis* enzyme except at its amino-terminus where the first fifteen amino acids are encoded by the *B. stearothermophilus* gene. This strong similarity between the hybrid 4 protein and the *B. stearothermophilus* protein may account for their similar resistance to heat inactivation. In contrast, hybrid D protein retains only 10% of its activity after incubation for 120 min. at 90° C. This polypeptide is highly chimeric in that approximately its entire amino terminal half is encoded by the *B. stearothermophilus* gene whereas the carboxyl-terminal half is encoded by DNA from the *B. licheniformis* gene (see FIG. 6). Since the thermostability of the hybrid 4 protein is less than that of either parent it may be that an interaction(s) between the amino-terminal and carboxy-terminal halves of alpha amylases are required for thermal stability and that these interactions are altered in the hybrid protein. The protein from hybrid 6 retains about 50% of its activity after incubation at 90° C. for 120 min., and therefore has the same thermostability as the parental *B. stearothermophilus* enzyme. The hybrid 6 protein is composed primarily of residues encoded by the *B. licheniformis* gene but the amino-terminal 73 residues are those of the *B. stearothermophilus* protein (see FIG. 6). This heterologous amino-terminus may have a slightly destabilizing effect on the protein structure thus possibly contributing to its reduced stability in comparison to the parental *B. licheniformis* enzyme. These results show that hybrid alpha amylases can be expected to show a range of thermostabilities which may be the same or different from those of the parental enzymes.

Figure 7:
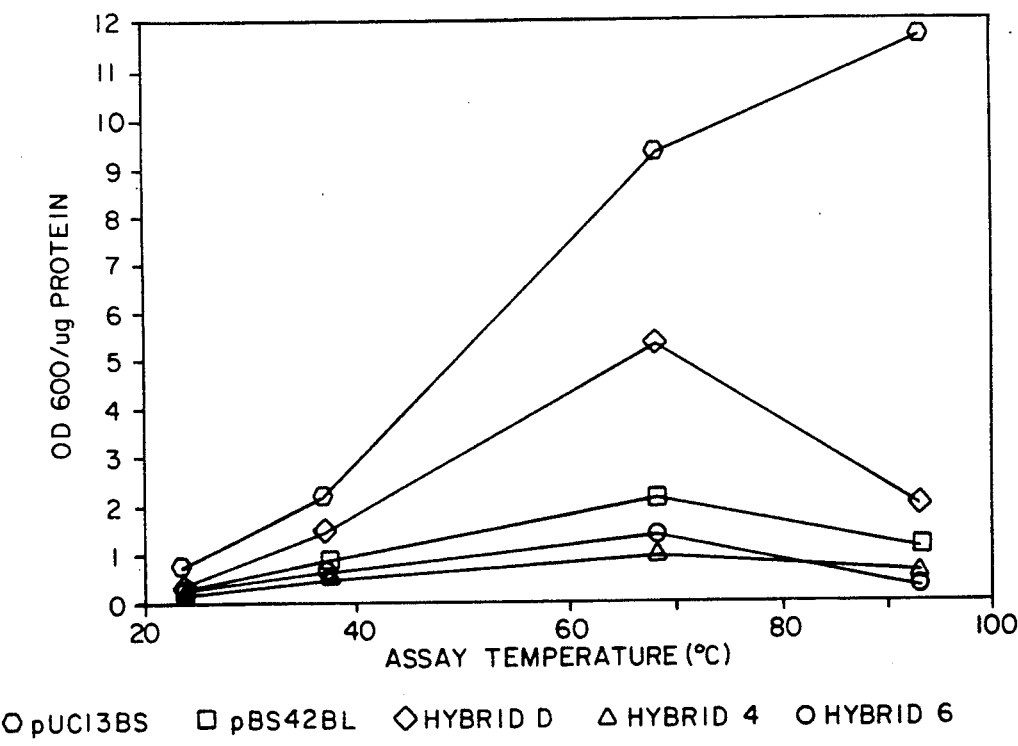
FIG. 7 depicts the specific activity of various hybrid alpha amylases at various temperatures.

The specific activities of the parental and hybrid alpha amylases purified as described above were also determined at four different temperatures. These data are shown in FIG. 7. The parental *B. stearothermophilus* enzyme has the highest specific activity at all temperatures, whereas the parental *B. licheniformis* enzyme is much less active at all temperatures. The hybrids 4 and 6 which as described above, contain only short stretches of amino-terminal residues derived from the *B. stearothermophilus* gene more closely resemble the *B. licheniformis* enzyme in their specific activity profiles. Hybrid D alpha amylase, however, has specific activities intermediate between those of the parental enzymes. The apparent large reduction of activity of this enzyme at 90° C. compared to 70° C. may be largely due to its marked instability at 90° C. as noted above. These data indicate that hybrid alpha amylases show a variety of specific activities.

EXAMPLE 4

In another preferred embodiment, hybrid alkaline proteases derived from *B. subtilis* and *B. amyloliquefaciens* were produced. A synthetic oligonucleotide sequence containing more than one unique restriction site was used to link DNA sequences encoding the *B. subtilis* and *B. amyloliquefaciens* alkaline proteases. Treatment of vector with endonucleases specific for each unique restriction site after recombination in a rec positive microorganism reduced background transformation by non-recombined vector.

Figure 4:
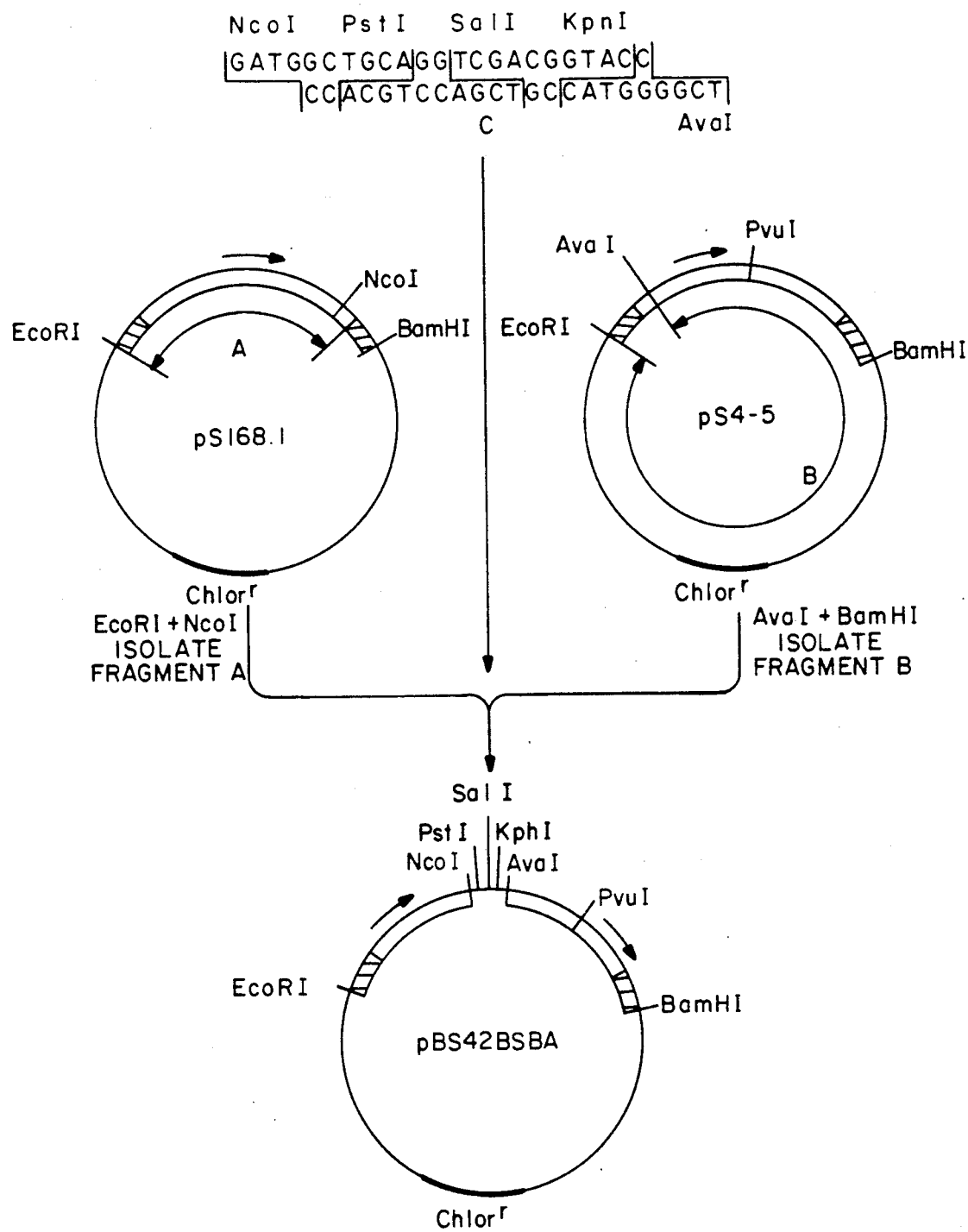
FIG. 4 depicts the construction of a plasmid containing DNA sequences encoding alkaline proteases from *B. subtilis* and *B. amyloliquefaciens* which are separated by a synthetic oligonucleotide containing three unique restriction sites.

A. Construction of the *B. subtilis* -*B. amyloliquefaciens* alkaline protease hybrid precursor plasmid pBS42BSBA As depicted in FIG. 4 the plasmid pS168.1 (44,32) containing the *B. subtilis* alkaline protease gene was digested with EcoRI and NcoI. The smaller fragment (fragment A) was isolated. The plasmid pS4-5 (44,33) containing the entire *B. amyloliquefaciens* alkaline protease gene was digested with EcoRI and AvaI. The larger vector fragment (fragment B) was isolated. Two complimentary synthetic oligonucleotides containing NcoI and AvaI cohesive termini and PstI, Sal I, and KpnI sites between these termini were annealed to form fragment C by heating at 95° C. and cooling to 23° C. Fragments A, B, and C were joined by ligation. The thus ligated vector was used to transform *E. coli* 294. A chloramphenicol resistant colony containing the plasmid pBS42BSBA was saved. *B. subtilis* strain BG2036 (44) contains deletions of the chromosomal alkaline protease and neutral protease genes. Strain BG2036 produced no protease when transformed with pBS42BSBA as determined by its failure to produce a halo of clearing on LB plates containing 0.1% skim milk. This result was expected because the plasmid lacks the carboxy-terminal codons of the *B. subtilis* alkaline protease gene and the amino-terminal codons of the *B. amyloliquefaciens* alkaline protease gene. In addition the codons of the latter gene are not in the same reading frame as those of the former gene. In contrast *B. subtilis* strain BG2036, containing either plasmid pS168.1 or pS4-5, produced active alkaline protease as determined by the production of halos of clearing on LB-skim milk agar plates. This result was expected because these latter two plasmids contain complete alkaline protease genes. It should be noted here that *E. coli* 294 transformed with pS168.1, pS4-5 or pBS42BSBA produced no alkaline protease as determined by a lack of halo production on LB skim milk agar plates. This may indicate that Bacillus alkaline protease promoters are not active in *E. coli* although other explanations are possible.

B. Generation of hybrid alkaline protease DNA sequences and expression of hybrid proteins One ng of plasmid pBS42BSBA was used to transform *E. coli* 294. The reaction was plated on LB chloramphenicol agar plates. About $2 \times 10^3$ colonies were obtained. Unlike the case for alpha amylases, alkaline proteases are not expressed in *E. coli*, even from complete genes. In order to determine whether recombination had occurred between the homologous regions comprising about 1 kb of the alkaline protease gene fragments of *B. subtilis* and *B. amyloliquefaciens* present on the plasmid it was necessary to use a hybridization technique. In the hybridization experiment we tested for the presence of fragment C in the plasmids contained in the transformants. We reasoned that if recombination between the DNA sequences had occurred then in all cases the sequences comprising fragment C would be deleted, whereas unrecombined plasmids would still contain these sequences. The hybridization experiment was performed as follows. The colonies were lifted from the plates on nitrocellulose filters. The filters were then prepared for hybridization by standard methods (27). Hybridization was carried out at low stringency by standard methods. The probe used was the sense (upper) strand of fragment C end-labelled with $\gamma^{32}$P-ATP and T4 polynucleotide kinase (34). By this method about $1.0 \times 10^3$ colonies were tested. Three were found which did not hybridize to the probe and were therefore presumed to contain plasmids in which recombination between the two partially homologous alkaline protease gene fragments had occurred.

EXAMPLE 5

In another experiment enrichment of such putative recombinants was achieved by predigestion of a plasmid preparation derived from BS42BSBA transformed *E. coli* 294. The plasmid preparation was digested with a combination of the restriction enzymes PstI, SalI, and KpnI prior to transformation of *E. coli* 294. 3 ng of plasmid thus digested gave rise to eight chloramphenicol resistant transformants. These colonies were tested by the hybridization procedure described above for the presence of the nucleotide sequence contained in fragment C. Seven of these colonies failed to hybridize and were therefore presumed to contain plasmids in which recombination between the two partially homologous gene sequences had occurred. In order to test whether the negatively hybridizing colonies contained plasmids which contained hybrid genes encoding active hybrid alkaline proteases, these plasmids were isolated and transformed into *B. subtilis* BG2036. This strain produced a zone of clearing on LB skim milk chloramphenicol agar plates upon transformation with any of the plasmids postulated to contain recombined alkaline protease hybrid genes. In contrast the putative unrecombined pBS42BSBA plasmids (8 isolates tested) failed to confer upon strain BG2036 transformants the ability to produce active alkaline protease as indicated by their failure to produce clearing zones on skim milk plates.

EXAMPLE 6

A. Characterization of hybrid DNA sequences contained in alkaline protease producing pBS42BSBA transformants of *E. coli* 294

The assumption was made that the alkaline protease positive colonies arose as a result of single crossover events within the pBS42BSBA plasmid between the *B. subtilis* and *B. amyloliquefaciens* DNA sequences which were initiated in a region in which they have sequence homology. It was reasoned that such recombined genes would contain 5' sequences contributed by the *B. subtilis* gene and 3' sequences contributed by the *B. amyloliquefaciens* gene. Early crossovers would be expected to contain larger 3' sequences contributed by the *B. amyloliquefaciens* genes whereas small segments of 3' sequences of the *B. amyloliquefaciens* gene would be present in later crossovers. There is a unique PvuII site present in pBS42BSBA which occurs within the *B. amyloliquefaciens* alkaline protease coding sequence (see FIG. 4). Crossovers in which the 3' region contributed by the *B. amyloliquefaciens* gene extended 5' of the PvuII site would result in plasmids with a unique PvuII site. Furthermore, this PvuII site would be located closer to the unique EcoRI site (located 5' of the promoter) than in pBS42BSBA plasmids which had not recombined. Putative hybrids 2, 6, 7, and 8 digested with EcoRI and PvuII showed a restriction pattern that indicated that the PvuII site was present. In contrast, crossovers in which the 3' region contributed by the *B. amyloliquefaciens* gene did not extend 5' to the PvuII site would result in plasmids without PvuII sites. Putative hybrids 1, 3, and 4 belong to this latter category as evidenced by their resistance to digestion with PvuII. These data indicate that early and late crossovers were present in the plasmids containing the putative hybrid alkaline protease genes.

B. Analysis of hybrid alkaline proteases encoded by hybrid alkaline protease DNA sequences For preliminary characterization of the hybrid proteins produced by *B. subtilis* BG2036 containing plasmids encoding the hybrid alkaline protease genes described above, the Km's were determined using a synthetic substrate. Crude culture supernatants were used as the source of enzyme. The substrate used was succinyl-L-ala-L-ala-L-pro-L-tyr-L-para-nitroanalide. The release of the product paranitroanalide was monitored coliometrically by measurement of absorbance at 430 nm using a Hewlett-Packard Diode Array Spectrophotometer Model 8451A. The Km's of the parental *B. subtilis* and *B. amyloliquefaciens* enzymes were also determined. The results of this study are shown in Table 2.

TABLE 2

Km's of parental and hybrid alkaline proteases on the synthetic substrate succinyl-L-ala-L-ala-L-pro-L-tyr-L-para-nitroanalide[1]

| Plasmid | Km (M × 10$^5$) |
| --- | --- |
| pS4-5 | 2.38 (±.09) |
| pS168.1 | 3.39 (±.15) |
| hybrid 1 | 5.54 (±.10) |
| hybrid 2 | 5.12 (±.10) |
| hybrid 3 | 5.42 (±.06) |
| hybrid 4 | 5.39 (±.11) |
| hybrid 6 | 2.86 (±.13) |
| hybrid 7 | 5.42 (±.12) |
| hybrid 8 | 2.75 (±.08) |

[1]host cell in all cases was *B. subtilis* BG2036.

It is evident that the hybrid enzymes fall into two basic classes. The first class, represented by hybrids 1,2,3,4 and 7 has Km's that are somewhat greater than that of either parental enzyme. The second class, represented by hybrids 6 and 8 has Km's that are intermediate between those of the parents.

These results show that the hybrid alkaline proteases have varying Km's for a particular synthetic substrate and that these differ from those of the parental enzymes. It is expected that determination of Km's using other synthetic substrates would also give a range of results and might also show varying favored substrates for the various hybrid enzymes.

EXAMPLE 7

In another preferred embodiment plasmids containing hybrid alpha amylase DNA sequences are selected by the post recombination transcription a tetracycline resistance determinant following excision of a transcription terminator as a result of homologous recombination between two parental alpha amylase DNA sequences.

A functional promoter is operably linked to *B. licheniformis* alpha amylase DNA sequences. A transcriptional terminator is placed 3' to this gene and 5' to DNA sequences encoding *B. stearothermophilus* alpha amylase A tetracycline resistance gene lacking its own promoter is placed just 3' to the *B. stearothermophilus* DNA sequence. Cells containing a plasmid with these characteristics would be sensitive to tetracycline because transcriptional read-through from the upstream active promoter is prevented by the transcription terminator. However if recombination between the two alpha amylase DNA sequences occurs the terminator will be excised thus allowing transcription of the tetracycline resistance gene. Cells containing plasmids in which this homologous recombination has occurred can be selected by resistance to tetracycline thus eliminating all background from unrecombined plasmids. This method is completely applicable for recombining any two homologous gene fragments.

Figure 8:
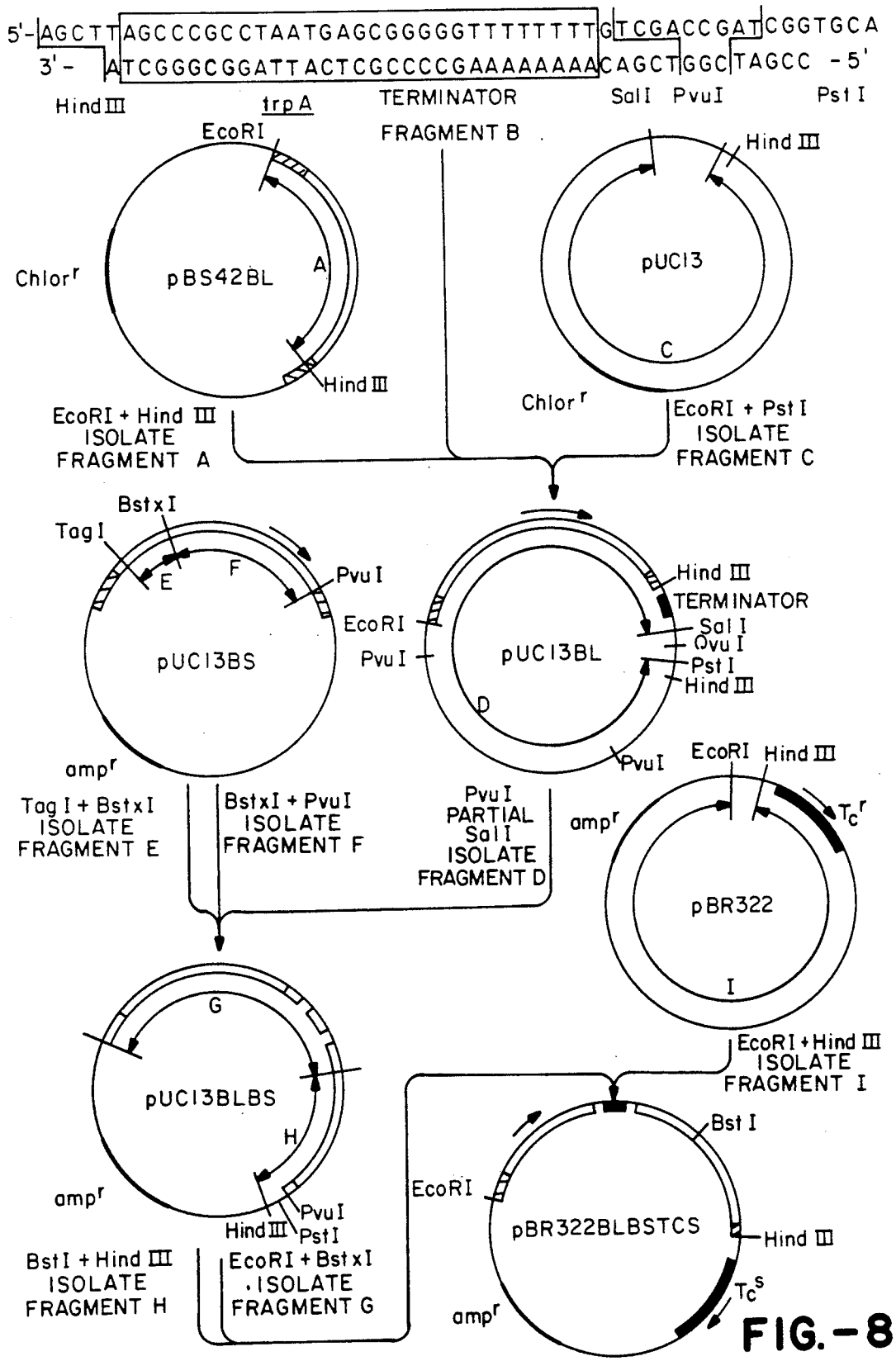
FIG. 8 depicts the construction of a plasmid containing DNA sequences encoding alpha amylases from *B. stearothermophilus* and *B. licheniformis* wherein the alpha amylase DNA sequences are separated by a synthetic transcription termination sequence and a DNA sequence encoding tetracycline resistance is positioned 3' to the sequences encoding the alpha amylase from *B. stearothermophilus*.

In order to use this method for selection of recombinant alpha amylase genes derived from the parental genes of *B. licheniformis* and *B. stearothermophilus* a plasmid is constructed as shown in FIG. 8. Plasmid pBS42BL which contains the complete *B. licheniformis* alpha amylase gene is cleaved with EcoRI and HindIII. The smaller fragment (fragment A) is isolated. Plasmid pUC13 is cleaved the EcoRI and PstI and the larger fragment (fragment C) is isolated. Two synthetic oligonucleotides are synthesized and then heated to 95° C. and cooled to 23° C. to allow annealing. The resulting fragment (fragment B) contains the *E. coli* trp transcription terminator (boxed) flanked on the 5' end by a HindIII site and on the 3' end by Sal I, PvuI, and PstI sites.

Fragments A, B, and C are joined by ligation and used to transform *E. coli* 294. Ampicillin resistant colonies contain the plasmid designated pUC13BL. This plasmid is digested completely with SalI and partially with PvuI. Fragment D is isolated. Plasmid pUC13BS is cleaved with TaqI and BstXI and the fragment (fragment E) is isolated. The same plasmid is cleaved with BstXI and PvuI and the smaller fragment (fragment F) is isolated. Fragments, D, E, and F are joined by ligation and used to transform *E. coli* 294. Ampicillin resistant transformants contain plasmid pUC13BLBS. This plasmid contains the entire *B. licheniformis* alpha amylase gene including its native promoter followed by the *E. coli* transcription terminator which is then followed by the coding sequence of the *B. stearothermophilus* gene which is complete except for the first eight codons. Plasmid pUC13BLBS is then cleaved with EcoRI and BstXI and the smaller fragment (fragment G) isolated. This plasmid is also cleaved with BstXI and HindIII and the fragment H isolated. The plasmid pBR322 is cleaved with EcoRI and HindIII and the larger vector fragment (fragmentI) isolated. Fragments G, H, and I are joined by ligation and transformed into *E. coli* 294. Ampicillin resistant transformants contain plasmid pBR322BLBSTCS. This plasmid differs most significantly from pUC13BLBS by the fusion of the coding region and ribosome binding site of the tetracycline resistance gene to the 3' end of the *B. stearothermophilus* alpha amylase coding region.

The replication of pBR322BSBLTCS in rec A positive *E. coli* 294 results in the excision of the transcription terminator by homologous recombination between the two alpha amylase DNA sequences. Expression of this recombinant plasmid results in transcription from the *B. licheniformis* alpha amylase gene promoter through the hybrid alpha amylase gene into the tetracycline resistance gene resulting in a polycistronic mRNA which is translated to give both the hybrid alpha amylase and the tetracycline resistance protein. Thus transformants containing such recombined plasmids can be selected by retransformation and selection on LB agar plates containing 5 ug/ml tetracycline.

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

The references grouped in the following bibliography and respectively cited parenthetically by number in the foregoing text, are hereby incorporated by reference.

What is claimed is:

1. An enzymatically active hybrid procaryotic alpha amylase comprising at least an amino-terminal amino acid sequence corresponding to an amino-terminal portion of the amino acid sequence of the alpha amylase of *B. stearothermophilus* and a carboxy-terminal amino acid sequence corresponding to a carboxy-terminal portion of the amino acid sequence of the alpha amylase of *B. licheniformis*.

2. The hybrid procaryotic alpha amylase of claim 1 wherein said amino-terminal and carboxy-terminal sequences are joined in a region wherein the hybrid DNA encoding said hybrid procaryotic alpha amylase is derived from DNA which does not contain a naturally occurring restriction endonuclease site which permits formation of said hybrid DNA.

3. An enzymatically active hybrid procaryotic alkaline protease comprising at least an amino-terminal sequence corresponding to a portion of the amino acid sequence of the alkaline protease of *B. subtilis* and a carboxy-terminal sequence correspond to a portion of the amino acid sequence of the alkaline protease of *B. amyloliquefaciens*.

4. The hybrid procaryotic alkaline protease of claim 3 wherein said amino-terminal and carboxy-terminal sequences are joined in a region wherein the hybrid DNA encoding said hybrid procaryotic alkaline protease is derived from DNA which does not contain a naturally occurring restriction endonuclease site which permits formation of said hybrid DNA.

5. An enzymatically active hybrid procaryotic amylase encoded by a hybrid DNA sequence, said hybrid DNA sequence being produced by a process comprising;

forming a circular vector comprising a replicable DNA sequence, a first DNA sequence encoding at least one amino acid of the amino-terminal portion of said hybrid amylase, a second DNA sequence encoding at least one amino acid of the carboxy-terminal portion of said hybrid amylase and a third DNA sequence between said first and second DNA sequences;

transforming a rec positive microorganism with said vector to produce a cell population containing a multiplicity of said circular vector and permitting crossover recombination within at least one of said vectors to excise said third DNA sequence to form a recombined circular vector having a hybrid DNA sequence comprising said first and said second DNA sequences encoding said enzymatically active hybrid amylase; and, and detecting expression of said hybrid DNA sequence by assaying for amylase activity.

6. An enzymatically active hybrid procaryotic amylase encoded by a hybrid DNA sequence, said hybrid DNA sequence being produced by a process comprising;

forming a circular vector comprising a replicable DNA sequence, a first DNA sequence comprising a functional promoter operably linked to sequences encoding at least one amino acid of the amino-terminal portion of said hybrid amylase, a second DNA sequence encoding at least one amino acid of the carboxy-terminal portion of said hybrid amylase and a third DNA sequence between said first and said second DNA sequences, said third DNA sequence comprising a DNA sequence which prevents the expression of said second DNA sequence;

transforming a rec portion microorganism with said circular vector to produce a cell population containing a multiplicity of said circular vector and permitting crossover recombination within at least one or said circular vectors to excise said third DNA sequence to form a recombined circular vector having a hybrid DNA sequence comprising said first and said second DNA sequences encoding said enzymatically active hybrid amylase; and detecting the expression of said hybrid DNA sequence by assaying for amylase activity.

7. An enzymatically active hybrid procaryotic amylase encoded by a hybrid DNA sequence, said hybrid DNA sequence being produced by a process comprising;

forming a circular vector comprising replicable DNA sequence, a first DNA sequence comprising a functional promoter operably linked to sequences encoding at least one amino acid of the amino-terminal portion of said hybrid amylase, a second DNA sequence encoding at least one amino acid of the carboxy-terminal portion of said hybrid amylase, a third DNA sequence between said first and said second DNA sequences, said third DNA sequence comprising a DNA sequence which prevents the expression of said second DNA sequence and a fourth DNA sequence 3' to said second DNA sequence, said fourth DNA sequence encoding a defined selection characteristic;

transforming a rec positive microorganism with said circular vector to produce a cell population containing a multiplicity of said circular vector and permitting crossover recombination within at least one of said circular vectors to excise said third DNA sequence to form a recombined circular vector having a hybrid DNA sequence comprising said first, said second and said fourth DNA sequences encoding said enzymatically active hybrid amylase and said defined selection characteristic; and selecting transformants which express said defined selection characteristic of said fourth DNA sequence and detecting expression of said hybrid DNA sequence by assaying for amylase activity.

8. An enzymatically active hybrid procaryotic amylase encoded by a hybrid DNA sequence, said hybrid DNA sequence being produced by a process comprising;

forming a circular vector comprising a replicable DNA sequence, a first DNA sequence comprising a functional promoter operably linked to a sequence encoding at least one amino acid of the amino-terminal portion of said hybrid amylase corresponding to a first part of a first parental amylase sequence, a second DNA sequence encoding at least one amino acid of the carboxy-terminal portion of said hybrid amylase corresponding to a first part of a second parental amylase sequence and a third DNA sequence between said first and said second DNA sequence encoding a second part of said first parental amylase sequence and a second part of said second parental amylase sequence;

transforming a rec positive microorganism with said circular vector to produce a cell population containing a multiplicity of said circular vector rand permitting crossover recombination within at lest one of said circular vectors to excise said hybrid DNA sequence to form a recombined circular vector having a hybrid DNA sequence comprising said first and said second DNA sequences encoding said enzymatically active hybrid amylase; and identifying transformants containing said recombined circular vector by detecting expression of said hybrid DNA sequence by assaying for amylase activity.

9. An enzymatically active hybrid procaryotic protease encoded by a hybrid DNA sequence, said hybrid DNA sequence being produced by a process comprising;

forming a circular vector comprising a replicable DNA sequence, a first DNA sequence encoding at least one amino acid of the amino-terminal portion of said hybrid protease, a second DNA sequence encoding at least one amino acid of the carboxy-terminal portion of said hybrid protease and a third DNA sequence between said first and second DNA sequences;

transforming a rec positive microorganism with said vector to produce a cell population containing a multiplicity of said circular vector and permitting crossover recombination within at least one of said vectors to excise said third DNA sequence to form a recombined circular vector having a hybrid DNA sequence comprising said firs and said second DNA sequences encoding said enzymatically active hybrid protease; and, and detecting expression of said hybrid DNA sequence by assaying for protease activity.

10. An enzymatically active hybrid procaryotic protease encoded by a hybrid DNA sequence, said hybrid DNA sequence being produced by a process comprising;

forming a circular vector comprising a replicable DNA sequence, a first DNA sequence comprising a functional promoter operably linked to sequences encoding at least one amino acid of the amino-terminal portion of said hybrid protease, a second DNA sequence encoding at least one amino acid of the carboxy-terminal portion of said hybrid protease and a third DNA sequence between said first and said second DNA sequences, said third DNA sequence comprising a DNA sequence which prevents the expression of said second DNA sequence;

transforming a rec positive microorganism with said circular vector to produce a cell population containing a multiplicity of said circular vector and permitting crossover recombination within at least one or said circular vectors to excise said third DNA sequence to form a recombined circular vector having a hybrid DNA sequence comprising said first and said second DNA sequences encoding said enzymatically active hybrid protease; and detecting the expression of said hybrid DNA sequence by assaying for protease activity.

11. An enzymatically active hybrid procaryotic protease encoded by a hybrid DNA sequence, said hybrid DNA sequence being produced by a process comprising;

forming a circular vector comprising a replicable DNA sequence, a first DNA sequence comprising a functional promoter operably linked to sequences encoding at least one amino acid of the amino-terminal portion of said hybrid protease, a second DNA sequence encoding at least one amino acid of the carboxy-terminal portion of said hybrid protease, a third DNA sequence between said first and said second DNA sequences, said third DNA sequence comprising a DNA sequence which prevents the expression of said second DNA sequence and a fourth DNA sequence 3' to said second DNA sequence, said fourth DNA sequence encoding a defined selection characteristic;

transforming a rec positive microorganism with said circular vector to produce a cell population containing a multiplicity of said circular vector and permitting crossover recombination within at least one of said circular vectors to excise said third DNA sequence to form a recombined circular vector having a hybrid DNA sequence comprising said first, said second and said fourth DNA sequences encoding said enzymatically active hybrid protease and said defined selection characteristic; and selecting transformants which express said defined selection characteristic of said fourth DNA sequence and detecting expression of said hybrid DNA sequence by assaying for protease activity.

12. An enzymatically active hybrid procaryotic protease encoded by a hybrid DNA sequence, said hybrid DNA sequence being produced by a process comprising;

forming a circular vector comprising a replicable DNA sequence, a first DNA sequence comprising a functional promoter operably linked to a sequence encoding at least one amino acid of the amino-terminal portion of said hybrid protease corresponding to a first part of a first parental protease sequence, a second DNA sequence encoding at least one amino acid of the carboxy-terminal portion of said hybrid protease corresponding to a first part of a second parental protease sequence and a third DNA sequence between said first and said second DNA sequence encoding a second part of said first parental protease sequence and a second part of said second parental protease sequence;

transforming a rec positive microorganism with said circular vector to produce a cell population containing a multiplicity of said circular vector and permitting crossover recombination within at lest one of said circular vectors to excise said third DNA sequence to form a recombined circular vector having a hybrid DNA sequence comprising said first and said second DNA sequences encoding said enzymatically active hybrid protease; and identifying transformants containing said recombined circular vector by detecting expression of said hybrid DNA sequence by assaying for protease activity.

* * * * *